(12) United States Patent
Chang et al.

(10) Patent No.: US 11,647,930 B2
(45) Date of Patent: May 16, 2023

(54) ELECTROCARDIOGRAPHY DEVICE

(71) Applicant: Quanta Computer Inc., Taoyuan (TW)

(72) Inventors: Chia-Yuan Chang, Taoyuan (TW); Jung-Wen Chang, Taoyuan (TW); Kao-Yu Hsu, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 863 days.

(21) Appl. No.: 16/237,878

(22) Filed: Jan. 2, 2019

(65) Prior Publication Data

US 2020/0069203 A1 Mar. 5, 2020

(30) Foreign Application Priority Data

Aug. 28, 2018 (TW) ................................. 107211722

(51) Int. Cl.
| | | |
|---|---|---|
| *A61B 5/25* | (2021.01) | |
| *A61B 5/00* | (2006.01) | |
| *A61B 5/30* | (2021.01) | |
| *A61B 5/316* | (2021.01) | |
| *A61B 5/333* | (2021.01) | |

(52) U.S. Cl.
CPC ................ *A61B 5/25* (2021.01); *A61B 5/30* (2021.01); *A61B 5/316* (2021.01); *A61B 5/6823* (2013.01); *A61B 5/333* (2021.01)

(58) Field of Classification Search
CPC .... A61B 5/25; A61B 5/28; A61B 5/30; A61B 5/316; A61B 5/6823; A61B 5/333
See application file for complete search history.

(56) References Cited

U.S. PATENT DOCUMENTS

| | | | |
|---|---|---|---|
| 2005/0101875 A1* | 5/2005 | Semler | A61B 5/282 600/509 |
| 2008/0139953 A1* | 6/2008 | Baker | A61B 5/14542 600/509 |
| 2013/0317333 A1* | 11/2013 | Yang | A61B 5/6833 600/300 |
| 2015/0087921 A1* | 3/2015 | Felix | A61B 5/6823 600/382 |
| 2016/0120433 A1* | 5/2016 | Hughes | G16H 80/00 600/483 |
| 2016/0359150 A1* | 12/2016 | de Francisco Martin | |
| 2018/0235501 A1* | 8/2018 | Nishimura | A61B 5/4266 A61B 5/259 |

* cited by examiner

*Primary Examiner* — Adam Z Minchella
(74) *Attorney, Agent, or Firm* — McClure, Qualey & Rodack, LLP

(57) ABSTRACT

An electrocardiography device is provided, including an adhesive assembly, a printed circuit board, two electrodes, a power supply assembly, and a sensing assembly. The printed circuit board is disposed on the adhesive assembly. The electrodes are connected to the circuit board and arranged along a first direction. The power supply assembly and the sensing assembly are disposed on the adhesive assembly and arranged along a second direction. The first direction is different from the second direction, and the power supply assembly is separate from the sensing assembly.

20 Claims, 7 Drawing Sheets

ELECTROCARDIOGRAPHY DEVICE

CROSS REFERENCE TO RELATED APPLICATIONS

This application claims the benefit of Taiwan Patent Application No. 107211722, filed Aug. 28, 2018, the entirety of which is incorporated by reference herein.

BACKGROUND OF THE INVENTION

Field of the Invention

The application relates in general to an electrocardiography device, and in particular, to a portable electrocardiography device.

Description of the Related Art

Electrocardiography (ECG) is the process of recording the electrical activity of the heart over a period of time using electrodes placed on the skin. This recording process is noninvasive.

In medicine, portable electrocardiography devices are widely used to obtain the electrical activity of the heart. The proper placement and connection of the electrocardiography electrodes is required if the correct electrical activity is to be obtained. However, conventional portable electrocardiography devices usually cannot be tightly attached to the chest of a human patient due to the limitations of the volume of the battery and the sensor. Therefore, how to address the aforementioned problem has become an important issue.

BRIEF SUMMARY OF INVENTION

To address the deficiencies of conventional products, an embodiment of the invention provides an electrocardiography device, including an adhesive assembly, a printed circuit board, two electrodes, a power supply assembly, and a sensing assembly. The printed circuit board is disposed on the adhesive assembly. The electrodes are connected to the circuit board and arranged along a first direction. The power supply assembly and the sensing assembly are disposed on the adhesive assembly and arranged along a second direction. The first direction is different from the second direction, and the power supply assembly is separate from the sensing assembly.

In some embodiments, the first direction is substantially perpendicular to the second direction, and the distance between the electrodes is greater than the distance between the power supply assembly and the sensing assembly. The power supply assembly comprises a lower cover, an upper cover, and a power supply member. The lower cover is affixed to the adhesive assembly. The upper cover is detachably connected to the lower cover to form an accommodating space. The power supply member is disposed in the accommodating space, wherein the power supply member is a primary battery or a rechargeable battery.

In some embodiments, the sensing assembly comprises a base and a sensing member, the base is affixed to the adhesive assembly, and the sensing member is detachably connected to the base. The sensing member has a top surface, a bottom surface, and a pressing portion, the top surface is opposite to the bottom surface, and the pressing portion is formed on the top surface, wherein the distance between the top surface and the bottom surface is greater than the distance between the pressing portion and the bottom surface. The sensing member further has a connecting port, and the base has a block plate. When the sensing member is joined to the base, the block plate covers the connecting port. Furthermore, a conductive member can pass the base and connect to the printed circuit board.

In some embodiments, the adhesive assembly comprises a permeable layer and a protecting layer, and the printed circuit board is disposed between the permeable layer and the protecting layer. The electrodes are connected to the printed circuit board and exposed from the permeable layer.

BRIEF DESCRIPTION OF DRAWINGS

The invention can be more fully understood by reading the subsequent detailed description and examples with references made to the accompanying drawings, wherein.

DETAILED DESCRIPTION OF INVENTION

The making and using of the embodiments of the electrocardiography device are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Unless defined otherwise, all technical and scientific terms used herein have the same meaning as commonly understood by one of ordinary skill in the art to which this invention belongs. It should be appreciated that each term, which is defined in a commonly used dictionary, should be interpreted as having a meaning conforming to the relative skills and the background or the context of the present disclosure, and should not be interpreted in an idealized or overly formal manner unless defined otherwise.

Figure 1:
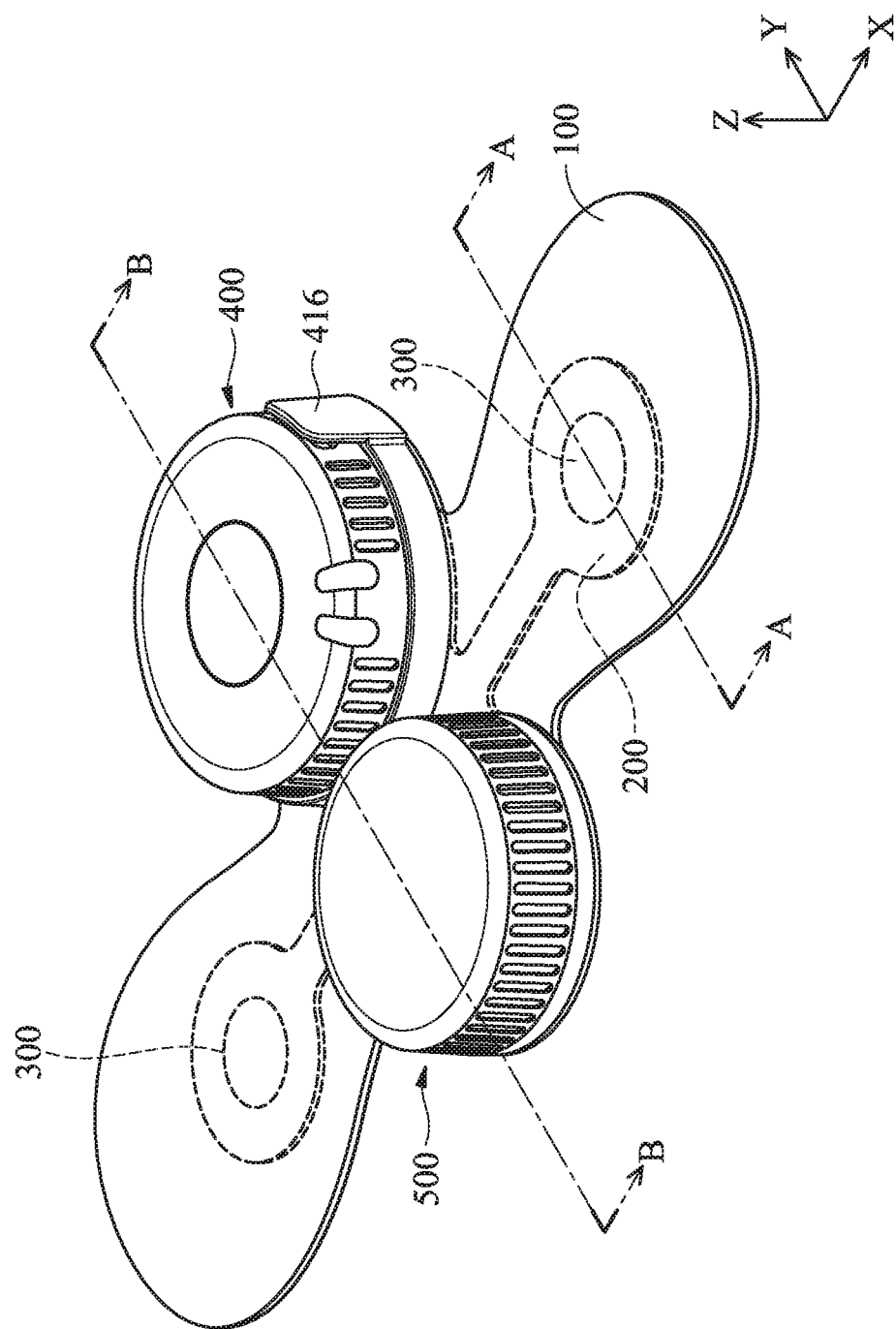
FIG. 1 is a schematic diagram of an electrocardiography device according to an embodiment of the invention.

Referring to FIG. 1, in an embodiment of the invention, an electrocardiography device E primarily comprises an adhesive assembly 100, a printed circuit board 200, two electrodes 300, a sensing assembly 400, and a power supply assembly 500. The sensing assembly 400 and the power supply assembly 500 can be disposed on the adhesive assembly 100 and electrically connected to the circuit board 200. Thus, the electric power required by the sensing assembly 400 can be provided by the power supply assembly through the circuit board 200.

Figure 2:
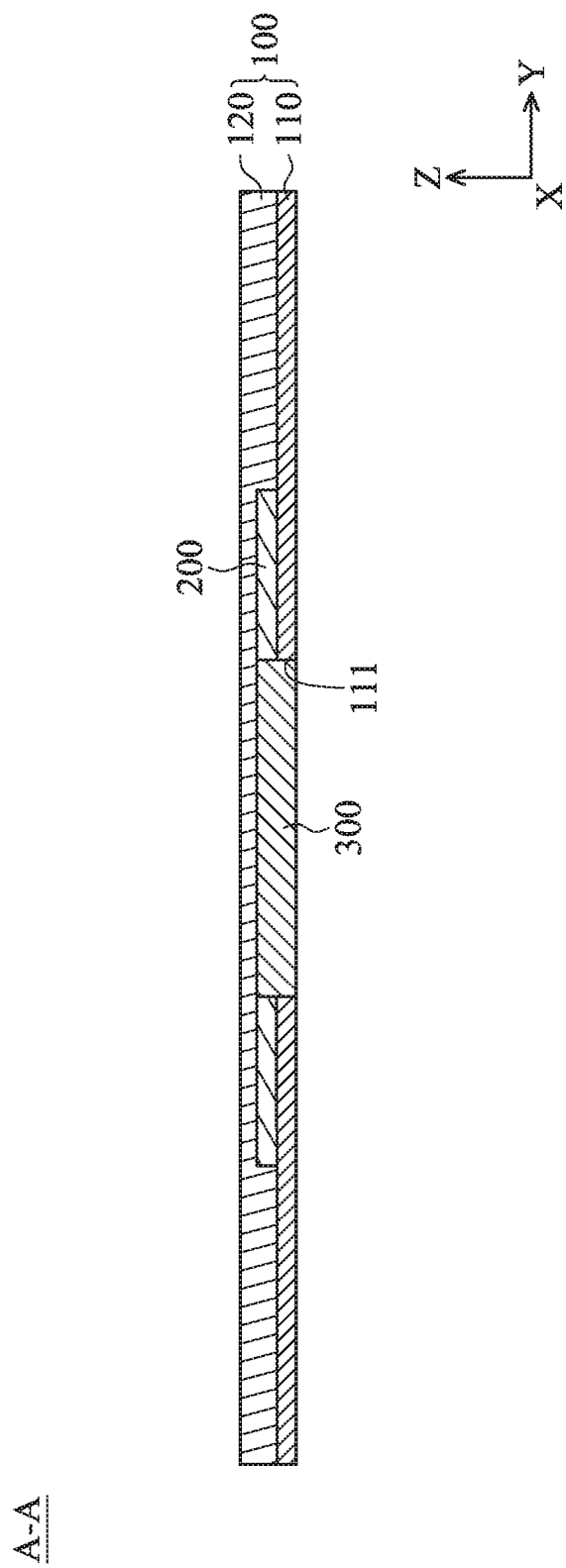
FIG. 2 is a cross-sectional view taken along line A-A of FIG. 1 according to an embodiment of the invention.

FIG. 2 is a cross-sectional view taken along line A-A of FIG. 1. In this embodiment, the adhesive assembly 100 comprises a permeable layer 110 and a protecting layer 120, and the printed circuit board 200 is disposed between the permeable layer 110 and the protecting layer 120. The permeable layer 110 has through holes 111, and each of the electrodes 300 can be exposed from the through holes 111 and electrically connected to the printed circuit board 200. The electrodes 300 can be aligned with the lower surface 112 of the permeable layer 110, so that the electrocardiography device E can achieve an integrated appearance, and the electrodes 300 can contact the human body when the electrocardiography device E is attached thereon.

The permeable layer 110 is adhesive, waterproof, and air permeable. For example, the permeable layer 110 can comprise polytetrafluoroethylene (PTFE), polyurethane (PU), polyethylene (PE), polystyrene (PS), polyvinyl chloride (PVC), polypropylene (PP), polymethyl methacrylate (PMMA), thermoplastic polyurethane (TPU), polyethylene terephthalate (PET), polyoxymethylene (POM), polycarbonate (PC), nylon, or a combination thereof, but it is not limited thereto. The protecting layer 120 can comprise a sponge. For example, the protecting layer 120 can comprise an ethylene vinyl acetate (EVA) sponge, polyurethane sponge, polyvinyl chloride sponge, latex sponge, or silica gel sponge, but it is not limited thereto.

Figure 3A:
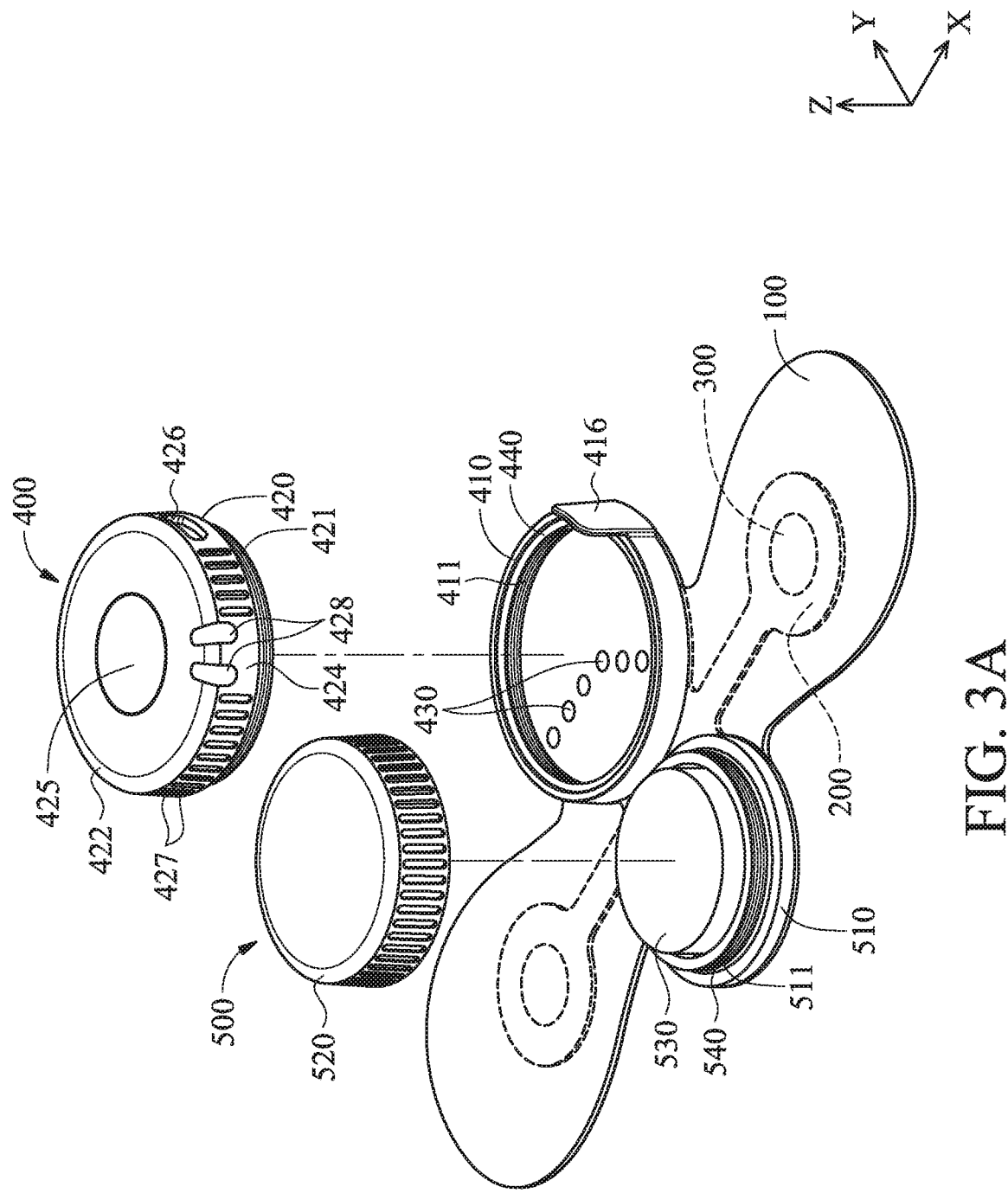
FIG. 3A is an exploded-view diagram of the electrocardiography device according to an embodiment of the invention.
Figure 3B:
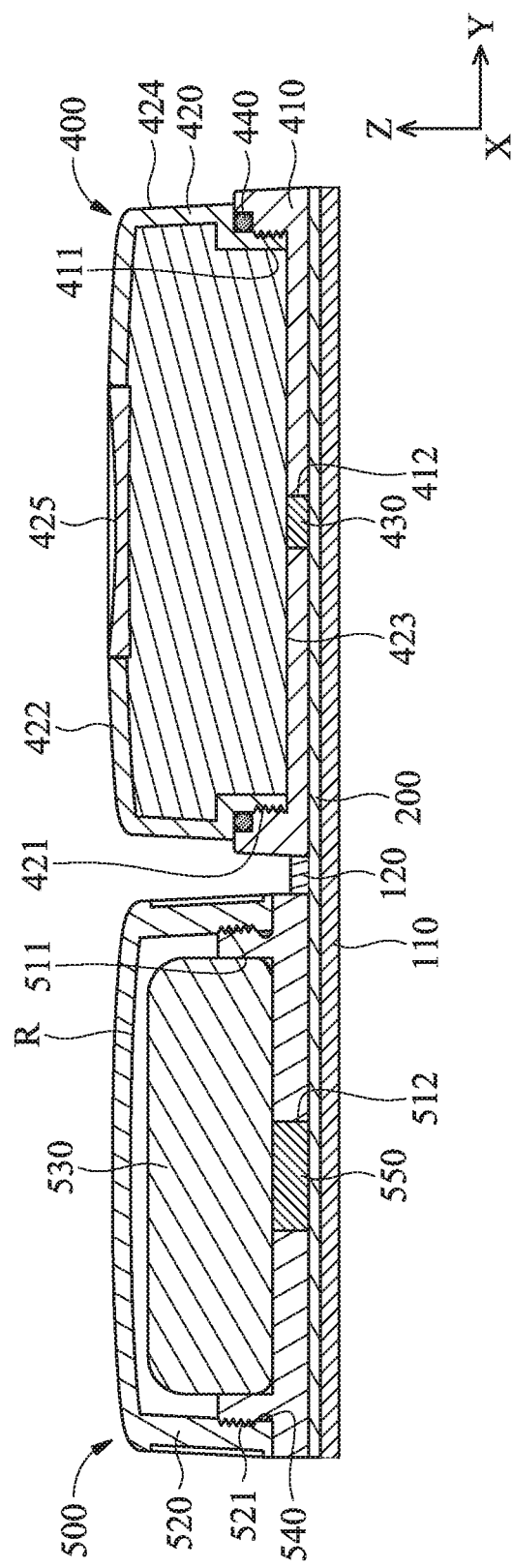
FIG. 3B is a cross-sectional view taken along line B-B of FIG. 1 according to an embodiment of the invention.

FIG. 3A is an exploded-view diagram of the electrocardiography device E in FIG. 1, and FIG. 3B is a cross-sectional view taken along line B-B of FIG. 1. As shown in FIGS. 3A and 3B, the sensing assembly 400 comprises a base 410 and a sensing member 420, wherein the base is affixed to the adhesive assembly 100, and the sensing member 420 is detachably connected to the base 410. For example, the base 410 and the sensing member 420 may have respective threaded portions 411 and 421 that correspond to each other. The sensing member 420 and the base 410 can be joined in a detachable manner by connecting the threaded portions 411 and 421.

One or more holes 412 can be formed on the base 410, and the conductive members 430 pass through the base 410 via the holes 412 and connect the printed circuit board 200 to form the contacts on the base 410, wherein the number of conductive members 430 corresponds to that of the holes 412. When the sensing member 420 is joined to the base 410, the sensing member 420 can contact the contacts (the conductive members 430), so as to electrically connect to the printed circuit board 200. Furthermore, an O-ring 440 can be disposed on the base 410. When the sensing member 420 is joined to the base 410, the O-ring 440 is situated between the sensing member 420 and the base 410, and the gap therebetween can be filled by the O-ring 440. Therefore, short-circuits and other damage to the members can be prevented by blocking water and foreign matter from entering.

The sensing member 420 has a top surface 422, a bottom surface 423, and a peripheral surface 424. The top surface 422 is opposite to the bottom surface 423, and the peripheral surface 424 connects the top surface 422 to the bottom surface 423. A pressing portion 425 is formed on the top surface 422. When the pressing portion 425 is pushed by an external force, the sensing member 420 can operate and record the measuring result into the memory unit (not shown) inside the sensing member 420. When the pressing portion 425 is pushed again, the sensing member 420 can stop operating.

In this embodiment, the pressing portion 425 is concave relative to the top surface 422. In other words, the distance between the top surface 422 and the bottom surface 423 is greater than the distance between the pressing portion 425 and the bottom surface 423. Therefore, when the electrocardiography device E is attached to the human body, the user can determine the position of the pressing portion 425 by contact even if the electrocardiography device E is covered by clothing.

Figure 3C:
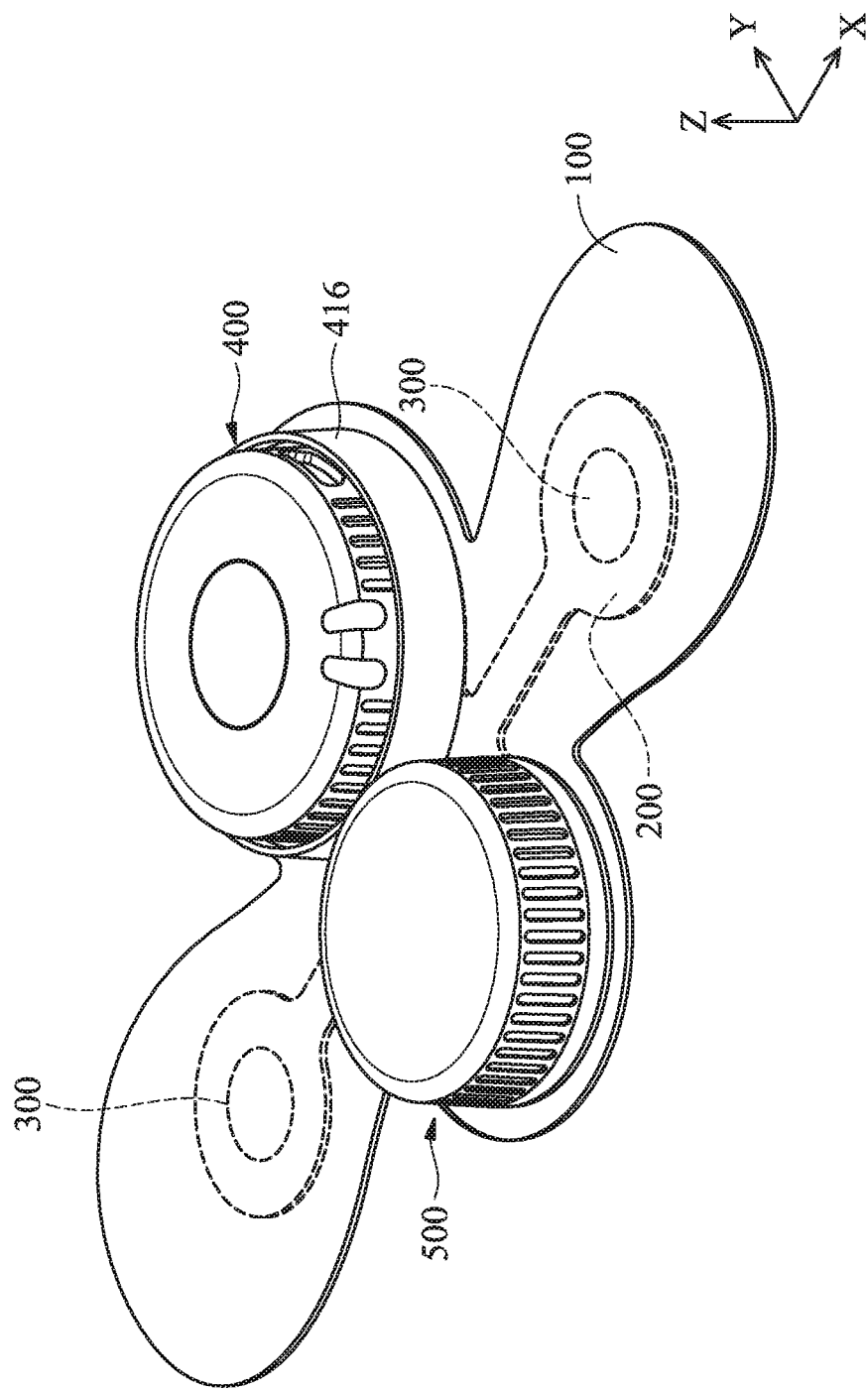
FIG. 3C is a schematic diagram of an electrocardiography device according to another embodiment of the invention.

A connecting port 426 is formed on the peripheral surface 424 of the sensing member 420. An external wire can be inserted into the connecting port 426 to connect the sensing member 420 to an external device (such as a computer), and the data in the sensing member 420 can be transmitted to the external device. For example, the connecting port 426 can be a universal serial bus (USB) connecting port. It should be noted that, in this embodiment, the base 410 has a block plate 416 that extends away from the adhesive assembly 100. When the sensing member 420 is joined to the base 410, the position of the block plate 416 corresponds to the position of the connecting port 426, and the block plate 416 covers the connecting port 426. Therefore, the user cannot insert the external wire into the connecting port 426 when the sensing member 420 operates, and short-circuits can be prevented. Moreover, foreign matter cannot enter the connecting port 426. Referring to FIG. 3C, in another embodiment, the block plate 416 surrounds the sensing member 420 and covers at least a portion of the connecting port 426, so as to prevent a situation wherein the block plate 416 does not correspond to the connecting port 426 due to tolerance or operator error.

As shown in FIGS. 3A and 3B, a plurality of slots 427 are formed on the peripheral surface 424 of the sensing member 420. The longitudinal axis of each of the slots 427 extends from the bottom surface 423 to the top surface 422 of the sensing member 420, and is substantially parallel to the normal direction of the base 410. The user can tightly hold the sensing member 420 by the slots 427, and easily rotate the sensing member 420 relative to the base 410.

Furthermore, one or more light-emitting diodes 428 can be formed on the sensing member 420. These light-emitting diodes 428 can emit different colors or frequencies according to the open/close and operation state of the sensing member 420.

Referring to FIGS. 3A and 3B, the power supply assembly 500 comprises a lower cover 510, an upper cover 520, and a power supply member 530. Similar to the sensing assembly 400, the lower cover 510 of the power supply assembly 500 is affixed to the adhesive assembly 100, and the upper cover 520 is detachably connected to the lower cover 510. For example, the lower cover 510 and the upper cover 520 may have respective threaded portions 511 and 521 that correspond to each other. The lower cover 510 and the upper cover 520 can be joined to form an accommodating space R. An O-ring 540 can be disposed between the lower cover 510 and the upper cover 520, and fill the gap therebetween, so as to prevent water and foreign matter from entering.

One or more holes 512 can be formed on the lower cover 510, and the conductive members 550 can pass through the lower cover 510 via the holes 512 and connect the printed circuit board 200 to form contacts on the lower cover 510, wherein the number of conductive members 550 corresponds to that of the holes 512. The power supply member 530 can be disposed in the accommodating space R and connected to the conductive members 550. Therefore, the power supply 530 can provide electric power to the sensing member 420 through the conductive members 550, the printed circuit board 200, and the conductive members 430 in sequence.

In this embodiment, the power supply member 530 is a primary battery, and can be directly affixed to the lower cover 510 and the conductive member 550 by welding. This can reduce the risk of departing of the power supply member 530. In some embodiments, the power supply member 530 can be a rechargeable battery. The user can take out the power supply member 530 when it has drained, and charge the power supply member 530 again.

Figure 4:
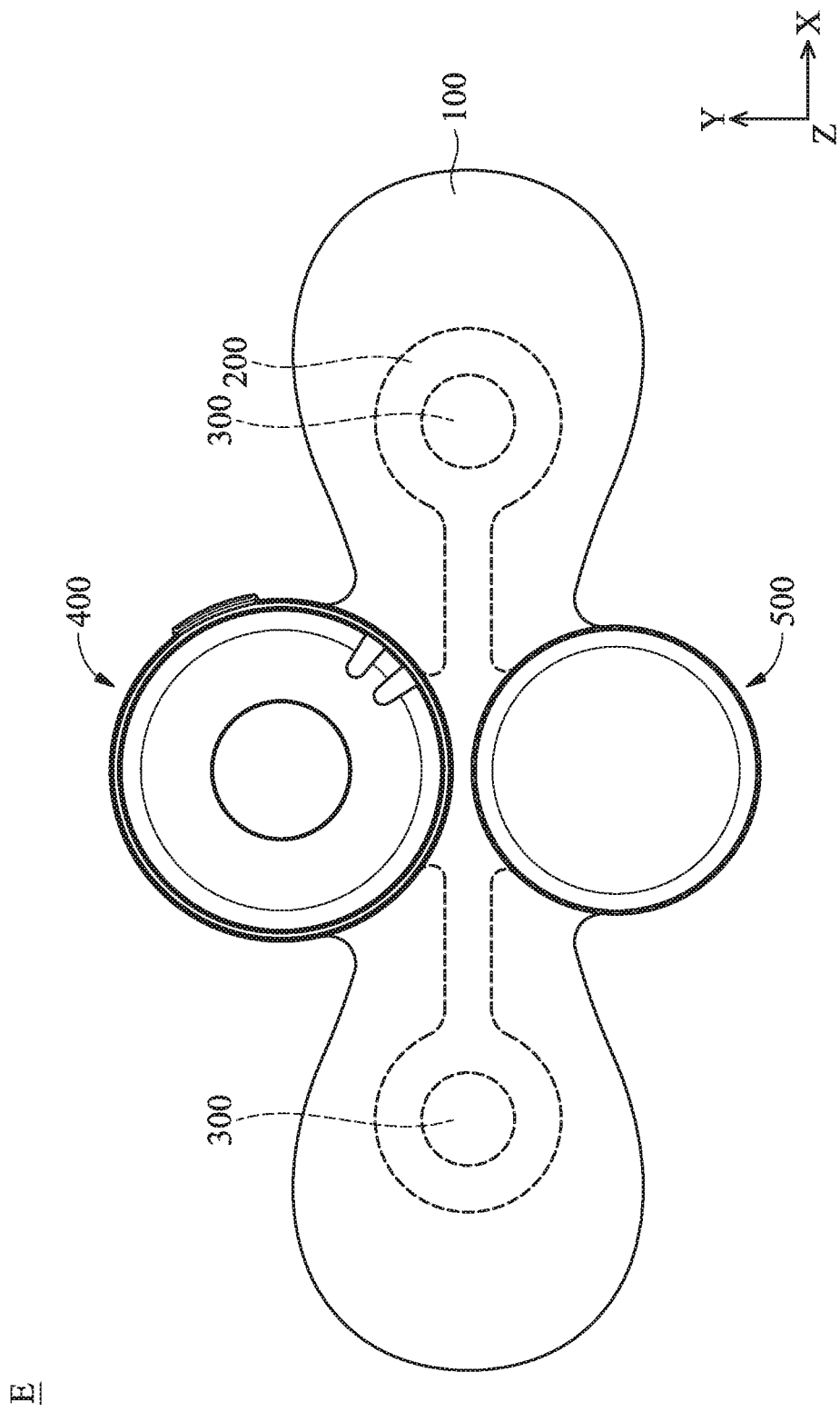
FIG. 4 is a top view of the electrocardiography device according to an embodiment of the invention.

Referring to FIG. 4, specifically, when the electrocardiography device E is assembled, two electrodes 300 are arranged along a first direction (X-axis), and the sensing assembly 400 and the power supply assembly 500 are arranged along a second direction (Y-axis). The distance between two electrodes 300 is greater than the distance between the sensing assembly 400 and the power supply assembly 500, and the sensing assembly 400 and the power supply assembly 500 are separated from each other (that is, a gap is formed therebetween). In this embodiment, the first direction is substantially perpendicular to the second direction. In some embodiments, the first direction is different from the second direction, but not perpendicular thereto. In other words, an obtuse angle can be formed between the first direction and the second direction.

Figure 5:
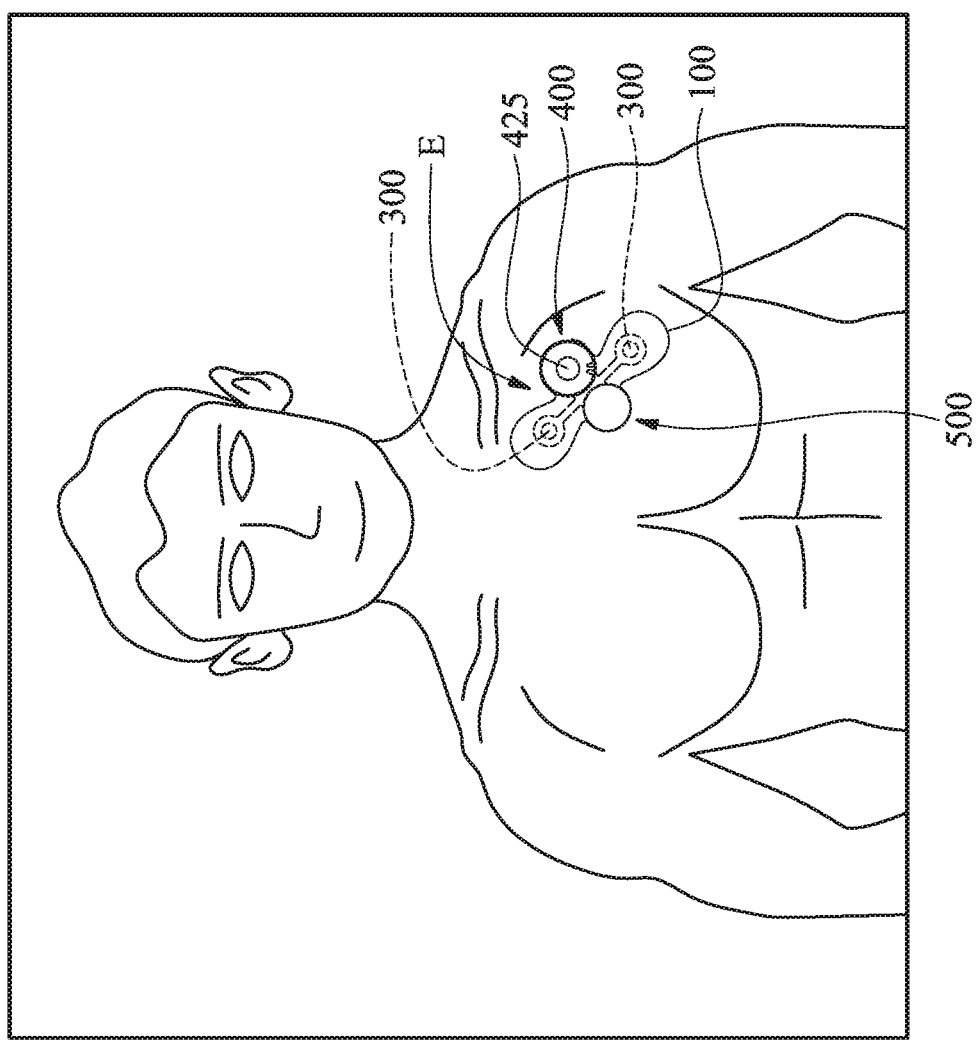
FIG. 5 is a schematic diagram of the electrocardiography device attached to a human body according to an embodiment of the invention.

The usage method of the electrocardiography device E is discussed below. When the electrocardiography device E is not in use, a releasing paper can be disposed on the surface of the permeable layer 110 of the adhesive assembly 100 facing outside, and another releasing paper can be also disposed on the protecting layer 120 of the adhesive assembly 100 facing outside. The adhesive assembly 100 is disposed between two releasing papers. As shown in FIG. 5, when the user needs to use the electrocardiography device E, he can detach the releasing papers from the adhesive assembly 100, and obliquely attach the electrocardiography device E onto the chest using the permeable layer 110, which is adhesive. The electrodes 300 can contact the human body. In particular, one of the electrodes 300 corresponds to the position of the heart, and the angle between the first direction between the two electrodes 300 and the longitudinal axis of the human body is between 30 and 60 degrees (such as 45 degrees).

Since the sensing assembly 400 and the power supply assembly 500 are separated from each other, the sensing assembly 400 and the power supply assembly 500 can be attached to the human body when the electrocardiography device E is attached to the human body via the adhesive assembly 100. A situation wherein the sensing assembly 400 or the power supply assembly 500 cannot be attached to the human body due to undulations of the chest will not happen.

When the user needs to use the electrocardiography device E to record the electrical activity of the heart (such as when the user is discomforted), he can push the pressing portion 425 of the sensing member 420, and the sensing member 420 can record the electrical activity of the heart. When the user wants to stop the recording of the electrocardiography device E, he can push the pressing portion 425 of the sensing member 420 again.

After recording, the user can separate the electrocardiography device E from the human body, and respectively separate the sensing member 420 and the upper cover 520 from the base 410 and the lower cover 510. In the interests of hygiene, the used adhesive assembly and the base 410 and the lower cover 510 thereon can be discarded. The sensing member 420 of the sensing assembly 400 and the upper cover 520 of the power supply assembly 500 can be recycled and re-used, so as to reduce medical waste.

If the power supply member 530 of the power supply assembly 500 is detachable (such as a rechargeable battery), the power supply member 530 can also be recycled and re-used. Furthermore, when the power supply member 530 of the electrocardiography device E needs to be changed during use, the upper cover 520 of the power supply assembly 500 can be separated from the lower cover 510. The old power supply member 530 can be taken out, and a new power supply member 530 can be put in. Subsequently, the upper cover 520 can be joined to the lower cover 510.

In summary, an electrocardiography device is provided, including an adhesive assembly, a printed circuit board, two electrodes, a power supply assembly, and a sensing assembly. The printed circuit board is disposed on the adhesive assembly. The electrodes are connected to the circuit board and arranged along a first direction. The power supply assembly and the sensing assembly are disposed on the adhesive assembly and arranged along a second direction. The first direction is different from the second direction, and the power supply assembly is separate from the sensing assembly.

Although some embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, compositions of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. Moreover, the scope of the appended claims should be accorded the broadest interpretation so as to encompass all such modifications and similar arrangements.

While the invention has been described by way of example and in terms of preferred embodiment, it should be understood that the invention is not limited thereto. On the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. An electrocardiography device, comprising:
   an adhesive assembly;
   a printed circuit board, disposed on the adhesive assembly;
   two electrodes, connected to the printed circuit board and arranged along a first direction;
   a power supply assembly, disposed on the adhesive assembly and connected to the printed circuit board; and
   a sensing assembly, disposed on the adhesive assembly and connected to the printed circuit board, wherein the power supply assembly and the sensing assembly are arranged along a second direction that is different from the first direction, and the power supply assembly is separated from the sensing assembly;

wherein the power supply assembly comprises a lower cover affixed to the adhesive assembly and an upper cover detachably connected to the lower cover to form a first accommodating space;

wherein the sensing assembly comprises a base affixed to the adhesive assembly, and the base comprises a second accommodating space;

wherein the first accommodating space is not communicated with the second accommodating space;

wherein the two electrodes are symmetrically disposed relative to a first imaginary axis that passes through the power supply assembly and the sensing assembly;

wherein a second imaginary axis that is perpendicular to the first imaginary axis and passes through the two electrodes is located between the power supply assembly and the sensing assembly, and the second imaginary axis does not intersect the power supply assembly and the sensing assembly.

2. The electrocardiography device as claimed in claim 1, wherein the first direction is substantially perpendicular to the second direction.

3. The electrocardiography device as claimed in claim 1, wherein the distance between the two electrodes is greater than the distance between the power supply assembly and the sensing assembly.

4. The electrocardiography device as claimed in claim 3, wherein the power supply assembly further comprises a power supply member disposed in the first accommodating space.

5. The electrocardiography device as claimed in claim 4, wherein the power supply member is a primary battery or a rechargeable battery.

6. The electrocardiography device as claimed in claim 1, wherein the sensing assembly further comprises a sensing member detachably connected to the base.

7. The electrocardiography device as claimed in claim 6, wherein the sensing member has a top surface, a bottom surface, and a pressing portion, the top surface is opposite to the bottom surface, and the pressing portion is formed on the top surface, wherein the distance between the top surface and the bottom surface is greater than the distance between the pressing portion and the bottom surface.

8. The electrocardiography device as claimed in claim 6, wherein the sensing member has a connecting port, and the base has a block plate, wherein when the sensing member is joined to the base, the block plate covers the connecting port.

9. The electrocardiography device as claimed in claim 6, wherein the electrocardiography device further comprises a conductive member, connected to the printed circuit board and passing the base.

10. The electrocardiography device as claimed in claim 1, wherein the adhesive assembly comprises a permeable layer and a protecting layer, and the printed circuit board is disposed between the permeable layer and the protecting layer.

11. An electrocardiography device, comprising:
an adhesive assembly;
a printed circuit board, disposed on the adhesive assembly;
two electrodes, connected to the printed circuit board and arranged along a first direction;
a power supply assembly, disposed on the adhesive assembly and connected to the printed circuit board; and
a sensing assembly, disposed on the adhesive assembly and connected to the printed circuit board, wherein the power supply assembly and the sensing assembly are arranged along a second direction that is different from the first direction, and the power supply assembly is separated from the sensing assembly;

wherein the sensing assembly comprises a sensing member, the sensing member has a top surface, a bottom surface, and a pressing portion, the top surface is opposite to the bottom surface, and the pressing portion is formed on the top surface;

wherein in a top view, the pressing portion does not overlap the power supply assembly, and the two electrodes, the power supply assembly, and the sensing assembly do not overlap each other;

wherein the printed circuit board comprises two openings, and the two electrodes are disposed in the two openings, respectively;

wherein the two electrodes are symmetrically disposed relative to a first imaginary axis that passes through the power supply assembly and the sensing assembly;

wherein a second imaginary axis that is perpendicular to the first imaginary axis and passes through the two electrodes is located between the power supply assembly and the sensing assembly, and the second imaginary axis does not intersect the power supply assembly and the sensing assembly.

12. The electrocardiography device as claimed in claim 11, wherein the first direction is substantially perpendicular to the second direction.

13. The electrocardiography device as claimed in claim 11, wherein the distance between the two electrodes is greater than the distance between the power supply assembly and the sensing assembly.

14. The electrocardiography device as claimed in claim 13, wherein the power supply assembly comprises:
a lower cover, affixed to the adhesive assembly;
an upper cover, detachably connected to the lower cover to form an accommodating space; and
a power supply member, disposed in the accommodating space.

15. The electrocardiography device as claimed in claim 14, wherein the power supply member is a primary battery or a rechargeable battery.

16. The electrocardiography device as claimed in claim 11, wherein the distance between the top surface and the bottom surface is greater than the distance between the pressing portion and the bottom surface.

17. The electrocardiography device as claimed in claim 11, wherein the sensing assembly comprises a base affixed to the adhesive assembly, and the sensing member is detachably connected to the base.

18. The electrocardiography device as claimed in claim 17, wherein the sensing member has a connecting port, and the base has a block plate, wherein when the sensing member is joined to the base, the block plate covers the connecting port.

19. The electrocardiography device as claimed in claim 17, wherein the electrocardiography device further comprises a conductive member, connected to the printed circuit board and passing the base.

20. The electrocardiography device as claimed in claim 11, wherein the adhesive assembly comprises a permeable layer and a protecting layer, the printed circuit board is disposed between the permeable layer and the protecting layer, and the two electrodes are in contact with the permeable layer and the protecting layer.

* * * * *